Figure 1:
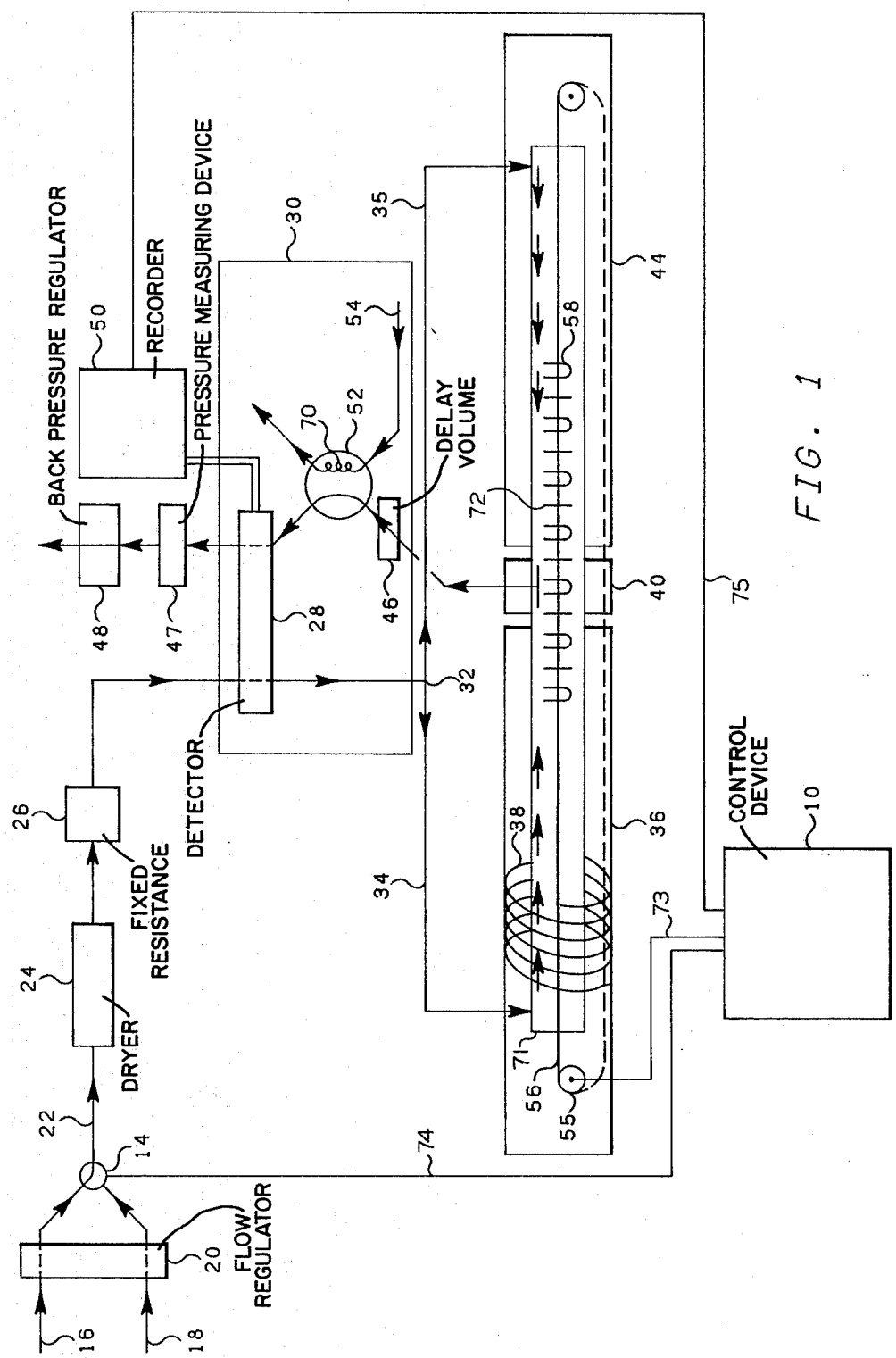

United States Patent [19]

Scott

[11] 4,335,610
[45] Jun. 22, 1982

[54] MULTI-SAMPLE SURFACE AREA MEASUREMENT

[75] Inventor: Richard L. Scott, Bartlesville, Okla.

[73] Assignee: Phillips Petroleum Company, Bartlesville, Okla.

[21] Appl. No.: 128,981

[22] Filed: Mar. 10, 1980

[51] Int. Cl.³ ............................................ G01N 15/08
[52] U.S. Cl. .................................... 73/432 PS; 73/38
[58] Field of Search .............................. 73/432 PS, 38

[56] References Cited

U.S. PATENT DOCUMENTS

| 2,692,497 | 10/1954 | Van Nordstrand | 73/432 PS X |
| 2,729,969 | 1/1956 | Innes | 73/432 PS X |
| 2,960,870 | 11/1960 | Nelsen et al. | 73/432 PS |
| 3,059,478 | 10/1962 | Coggeshall et al. | 73/432 PS |
| 3,203,252 | 8/1965 | Polinski et al. | 73/432 PS |
| 3,211,006 | 10/1965 | Haley, Jr. | 73/432 PS |
| 3,211,007 | 10/1965 | Atkins | 73/432 PS |
| 3,222,133 | 12/1965 | Ballou et al. | 73/432 PS X |
| 3,255,122 | 6/1966 | Constabaris et al. | 73/432 PS X |
| 3,262,319 | 7/1966 | Orr, Jr. et al. | 73/432 PS |
| 3,295,720 | 1/1967 | Slone | 73/432 PS X |
| 3,296,869 | 1/1967 | Bultemann | 73/432 PS |
| 3,299,713 | 1/1967 | Haul et al. | 73/432 PS |
| 3,306,112 | 2/1967 | Jenckel | 73/432 PS |
| 3,349,625 | 10/1967 | Benusa et al. | 73/432 PS |
| 3,464,273 | 9/1969 | Hendrix et al. | 73/432 PS |
| 3,482,452 | 12/1969 | Tabikh | 73/432 PS |
| 3,500,675 | 3/1970 | Sandstede et al. | 73/432 PS X |
| 3,509,762 | 5/1970 | Conway et al. | 73/104 |
| 3,555,912 | 1/1971 | Lowell | 73/432 PS |
| 3,707,870 | 1/1973 | Herve et al. | 73/38 |
| 3,732,736 | 5/1973 | Glaude et al. | 73/432 PS |
| 3,771,367 | 11/1973 | Lowell et al. | 73/432 PS |
| 3,783,697 | 1/1974 | Lowell et al. | 73/432 PS |
| 3,850,040 | 11/1974 | Orr, Jr. et al. | 73/432 PS |
| 3,884,083 | 5/1975 | Lowell | 73/432 PS |

FOREIGN PATENT DOCUMENTS 1129734  5/1962  Fed. Rep. of Germany ... 73/432 PS

Primary Examiner—Charles A. Ruehl
Assistant Examiner—Joseph W. Roskos

[57] ABSTRACT

The surface area of a plurality of samples is measured in an apparatus in which these samples are all included in a housing, subjected to adsorption of the adsorbing fluid and seriatim moved into a desorption zone in which one sample at a time is subjected to a desorption step. The apparatus and operation lends itself to automation.

17 Claims, 4 Drawing Figures

MULTI-SAMPLE SURFACE AREA MEASUREMENT

The present invention relates to an apparatus and a process for measuring the surface area of each of a plurality of samples. More specifically, the present invention relates to an apparatus and a process for carrying out surface area measurements on a plurality of samples in an automatized way.

BACKGROUND OF THE INVENTION

The surface area of materials is a property of great significance in several applications. Silica-alumina and carbon black are two examples of products where one of the important characteristics is the surface area. In several catalytically promoted reactions, the surface area of the catalyst determines not only the yield of the process, but in several instances, the reactions result and the chemical composition of the product made.

In view of the importance of the surface area, methods have been developed for an accurate determination thereof. One known method consists in contacting a weighed sample, the surface area of which is to be determined, with fluid which is adsorbed onto the surface area of the sample. The larger the surface area of the samples of the same weight will be, the larger the quantity of adsorbed fluid on such a sample will be. The so pretreated sample is then subjected to heat to effect desorption of the adsorbed fluid into a carrier gas stream. The carrier gas stream containing the desorbed adsorbing fluid is passed through a detector from which the amount of adsorbing fluid that has been desorbed from the samples in the carrier gas is measured, displayed, registered. Thereby the total quantity of desorbed adsorbing fluid can be determined and the surface area of the sample can be determined.

Whereas the process described is very accurate and effective, it is also a time consuming and labor intensive procedure. It would be desirable to have an apparatus and method available which allow the measurement of a multitude of samples and which lend themselves to automatic operation.

Therefore, it is one object of this invention to provide an apparatus for measuring the amount of a fluid desorbed from a plurality of samples. Another object of this invention is to provide a process for measuring the quantity of an adsorbing fluid desorbed on each of a plurality of samples without having to complete each and every step of the measurment on one sample before the next sample can be handled, but still using only one detecting device.

A further object of this invention is to provide means for automatic measurement of the surface area of a plurality of samples.

Figure 2:
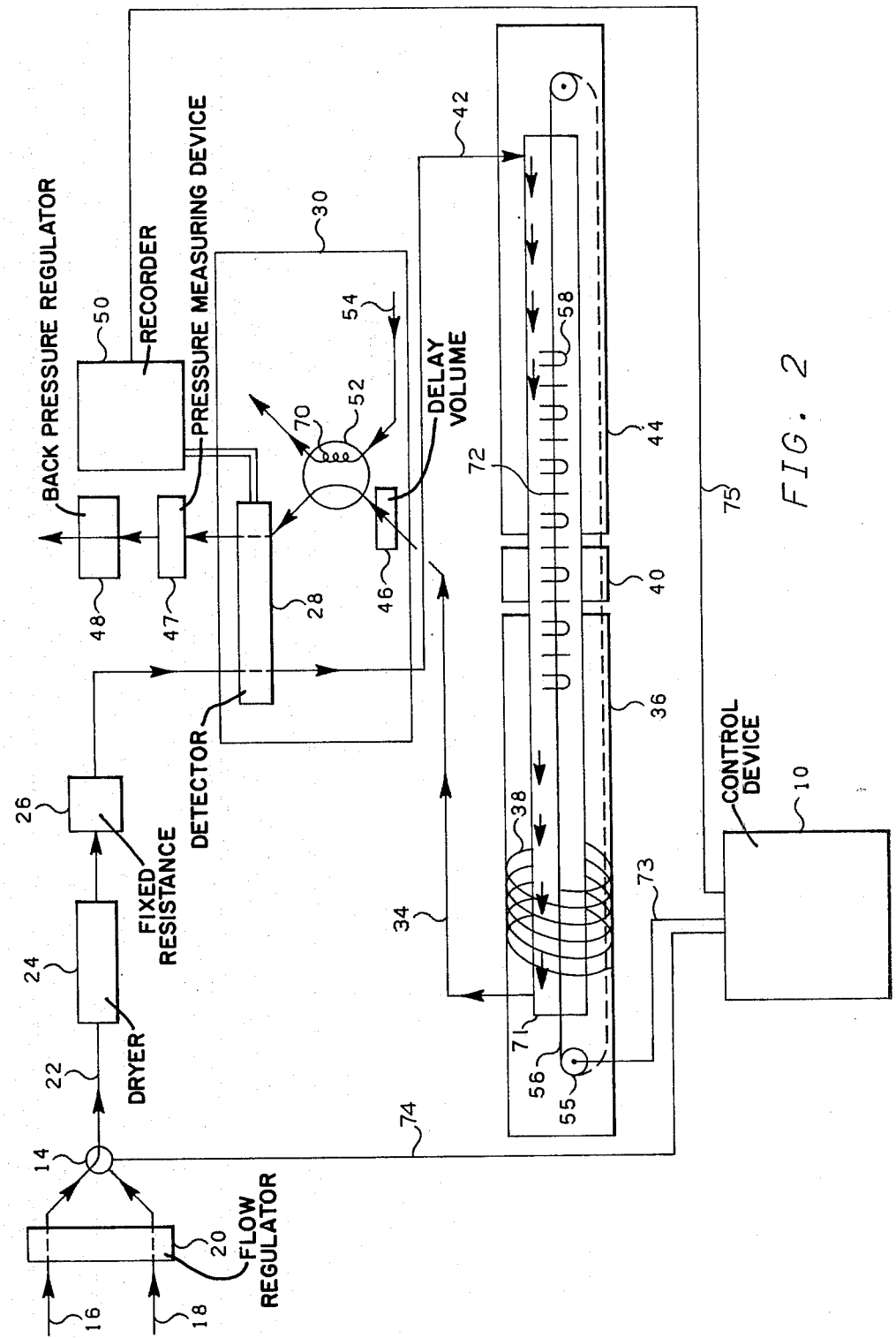
Figure 3:
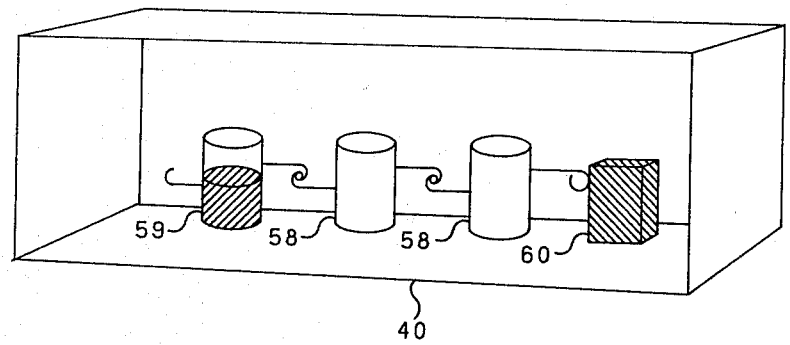
Figure 4:
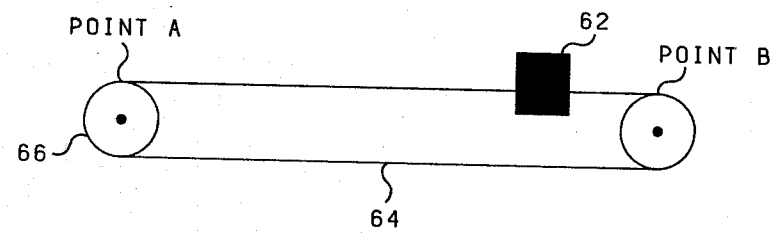

These and other objects, advantages, details, features and embodiments of this invention will become apparent to those skilled in the art from the following detailed description of the invention, the appended claims and the drawing in which FIG. 1 is a schematic representation of an apparatus of this invention for measuring surface areas of a plurality of samples, FIG. 2 shows another emodiment of this invention with one gas inlet to the housing and one gas outlet from the housing, FIG. 3 represents a schematic perspective view of a sample holder train with a pulling magnet, and FIG. 4 is a schematic representation of a mechanism for moving the sample supports through the various zones of this apparatus.

STATEMENT OF THE INVENTION

In accordance with this invention, an apparatus for measuring the amount of fluid adsorbed by a plurality of samples is provided. This apparatus comprises an adsorption zone and a desorption zone thermally insulated from each other in a housing. The adsorption zone is provided with means for exposing the samples to the fluid to be adsorbed, whereas the desorption zone is provided with means for causing the release of at least some of the fluid adsorbed from the sample. A detector is operatively connected to the desorption zone so that the quantity of fluid released from a sample can be determined. Transporting means are operatively associated with the adsorption and desorption zone to allow the transporation of the samples from the adsorption zone to the desorption zone. Preferably, the apparatus also comprises a drying zone within the housing so that the plurality of samples can be all first subjected to drying thereafter to adsorption and thereafter seriatim to desorption and measurement of the surface area.

Another embodiment of this invention resides in a process for determining the quantity of a fluid adsorbed by each of a plurality of samples. This process comprises the steps of adsorbing, desorbing and measuring the quantity of desorbed fluid. In accordance with this invention, the adsorption is simultaneously carried out on all of the samples and thereafter the samples are seriatim subjected to a desorption step and the desorbed fluid is passed to a detector wherein the quantity of desorbed fluid is determined for each of the samples.

Further details and preferred embodiments, both for the apparatus and for the process of this invention will become apparent from the following description of the drawing.

A train of sample holders 58 thermally separated from each other by heat shield units 72 is moveably arranged in an elongated housing 71 having removable closure means (not shown) at one of its ends which allow the sample train to be inserted and removed from the housing 71. Surrounding the housing 71 are three units 36, 40 and 44. The section of the housing 71 arranged within unit 36 is a drying zone. Unit 36 is provided with heating means such as coil 38 for applying heating energy to the samples in order to dry them.

The portion of the housing 71 located within unit 44 constitutes the adsorbing zone. Unit 44 is provided with cooling means (not shown) which allow the cooling of the samples in the sample holders 58 to a low temperature. Advantageously this can be achieved by cooling the section of the housing 71 located within unit 44 to liquid nitrogen temperature.

The section of the housing located within unit 40 constitutes the desorbing zone. Unit 40 is provided with heating means (not shown) which allow heating of the sample to release the adsorbed fluid the quantity of which is representative of the surface area of the sample.

The transporting means for moving the sample train from unit 36 into unit 44 and seriatim back into and out of unit 40 is shown as a conveyor belt or wire 56 driven by pulleys 55. Care must be taken in this embodiment to avoid the entraining of any extraneous gas through the space through which the conveyor 56 passes into the housing 71.

The surface area determination of the plurality of samples in the plurality of sample holders 58 is carried out as follows. The entire train of sample holders 58 with the samples therein is placed into the drying zone, i.e. the portion of housing 71 contained in unit 36. The samples are heated in this unit 36 to remove essentially all of the water from the surface areas of the samples. Thereafter, the sample train by means of the conveyor 56 is moved into the adsorption section, i.e. that portion of the housing 71 that is located within unit 44. In the adsorption section, the samples are cooled to a low temperature. The samples are exposed to the flow of a carrier gas such as helium or hydrogen containing an adsorbing fluid such as nitrogen, oxygen, argon, carbon dioxide, propane or n-butane.

The samples are exposed to the carrier gas and the adsorbing fluid for a time sufficient to equilibrate the adsorption of the adsorbing fluid on the sample surfaces of all the samples. Then the first sample is moved from the adsorbing zone into the desorption zone, i.e., the portion of the housing 71 arranged within unit 40. In the desorption zone, the sample is heated to a temperature where essentially all the adsorbing fluid is released from the sample (desorbed) and removed with the flowing carrier gas through the detector 28 for measuring the quantity of desorbed fluid as will be described later. After essentially all the adsorbed fluid has been released from one sample this sample is removed from the desorbing zone and the next and still cold sample is introduced into this zone. The desorbing procedure is repeated until essentially all of the adsorbed fluid has been removed from that sample. This sequence is repeated until all of the samples have been measured. Thereafter, the sample train if desired can be replaced by another sample train and the sequence of steps described can be repeated.

The gas inlet valve 14 is connected to two or more nitrogen-containing gas streams 16 and 18 of differing compositions and is actuated by controller 10. The purpose of this embodiment of the invention is to allow one to automatically obtain data on the adsorption of nitrogen upon the solid sample material from nitrogen-containing gas streams with differing partial pressures of nitrogen. Such a capability will allow the practitioner to obtain potentially more reliable surface area measurements by having two separate sets of data points upon which to base calculations. A flow regulator 20 provides for constant flow of carrier gas from line 22 through the apparatus. Valve 14 allows switching from one stream 16 to the other stream 18 and vice versa. The gas stream comprising the carrier gas and the adsorbing fluid-in the following referred to as the gas stream—then flows through a dryer 24 and a fixed resistance 26. This fixed resistance can consist of a tube packed with crushed fire brick or molecular sieve material. This fixed resistance can be arranged anywhere downstream of the flow regulator 20 and upstream of the detector 28. The function of this fixed resistance 26 is to provide a pressure drop, for example of 10 psi, in the system which results in an increased sensitivity of the apparatus.

The gas stream then flows through one branch of the thermal conductivity detector, a unit well known in the art. This thermal conductivity detector is very sensitive to any change of composition of the gas flowing through this detector. In FIG. 1 the gas stream at 32 is divided into two gas streams 34 and 35 entering the housing 71 at the opposing ends thereof. The two gas streams flow from the opposing ends inside of a housing 71 to the desorption zone located in unit 40 and leave the housing 71 at the desorption zone entraining all the desorbed fluid from the sample.

The gas containing the desorbed fluid is passed through a delay volume 46 and a gas valve 52 to the detector 28. The delay volume 46 has the function to prevent any overly rapid changes in the flow rate of the gas stream through the detector which might be interpreted as composition changes by the sensitive detector 28. The gas valve 52 allows the calibration of the instrument as will be described later.

The gas stream containing desorbed fluid has a different composition, namely a higher concentration of adsorbing fluid then the gas stream that was not exposed to a desorption of a sample. The thermal conductivity of the gas is therefore changed and the corresponding signal from the detector is generated and transmitted to a recorder 50. The gas is finally passed through a pressure measuring device 47 and a back pressure regulator 48.

In the preferred embodiment of this invention, an automatic control device 10 is provided for. This automatic control device receives a signal responsive to the measured gas stream composition via line 75 and generates manipulating signals to operate a motor driving the pulleys 55 via line 73 and thus to advance the samples to the various locations. Furthermore, the control device 10 generates a manipulating signal to operate valve 14 and this manipulating signal is provided via line 74.

The calibration of the detector 28 which is located within a temperature stabilized zone 30 is done as follows. A defined volume 70 is filled with adsorbing gas at a well defined pressure. Valve 52 is then turned 180° so that the gas flow coming from delay volume 46 will entrain the defined quantity of adsorbing gas. The output signal generated by the detector 28 is therefore responsive to a known quantity of adsorbing gas and from another signal, the unknown quantity can therefore be calculated. Plotting detector signal versus time results in a peak or bell shaped curve and the area under this curve is proportional to the quantity of desorbed gas passed through the detector 28.

Increased accuracy and greater reliability of the measurements can be achieved when the measurement is repeated with a gas stream having a different partial pressure of the adsorbing fluid. This is done by switching valve 14 and allowing the other gas stream to flow through the system.

Instead of a thermal conductivity detector 28, other detectors suitable for measuring the quantity of a desorbed fluid in a gas stream can also be used. Thus, flame ionization detectors can be used in connection with a carbon containing gas as the adsorbed gas. Examples of such carbon containing gases are propane and n-butane.

The apparatus of this invention as shown in the drawing has a linear elongated housing 71 containing the drying zone, the adsorption zone and the desorption zone. It is also possible and contemplated within this invention to arrange these zones along a circle. Although it is preferred to arrange the desorbing zone between the adsorbing and the drying zones any other arrangement is also contemplated by this invention.

The apparatus of this invention allows the automatic measurement of surface areas of the plurality of samples. Controller device 10 can be designed in such a way as to subject the first sample to drying, adsorbing and desorbing, thereafter to subject the next sample to drying, adsorbing and desorbing and so forth. Alternatively, it is contemplated to simultaneously dry all the samples, to simultaneously have all the samples adsorb the adsorbing gas and then seriatim subject the samples to the desorption step, one at a time. The controller device 10 can be operated so that the desorption of the samples is carried out at a constant time for each sample. Another way of operating the control device 10 is to generate a signal via line 73 for advancing the samples only after the signal from recorder 50 via line 75 has indicated that the signal from detector 28 has returned to the base line, i.e. that no detectable quantity of desorbed fluid is present in the gas stream anymore. The calculation of the surface area from the amount of desorbed fluid is well known in the art. For example, the BET equation can be used for this purpose.

Preferably, in accordance with this invention the output signal of the detector 28 is used in a computer of which control device 10 may be a portion. This computer may both store the information, carry out the integration, provide the control signals and perform any logical operations for which it may be programmed.

Temperature ranges for the drying zone, the adsorbing zone, the desorbing zone and the detector unit 30 are dependent, of course, on the nature of the adsorbing fluid. Typical temperature ranges are given in the following table:

TABLE I

| Zones | Temperature Range |
|---|---|
| Drying Zone | 100–300° C. |
| Adsorption Zone | −200–50° C. |
| Desorption Zone | 0–150° C. |
| Constant Temperature Zone 30 | 30–85° C. |

Another embodiment of this invention is shown in FIG. 2. In this embodiment, the fluid or gas stream is not split into two parallel streams which are reunited at the desorption zone as shown in FIG. 1, but rather the entire stream flows via conduit 42 into one end of the housing 71 and leaves the housing at the other end from where this gas stream flows via conduit 34 into the measuring unit 30. When the measurement is carried out according to this embodiment of the invention during the desorption step it is necessary to activate the heating means of drying zone 36 in order to prevent the desorbed gas (for instance, nitrogen) from the desorption zone from the sample, from being subsequently readsorbed by the solid samples in the drying zone which had previously been desorbed in the desorption zone.

In FIGS. 3 and 4 portions of the presently preferred transporting means are illustrated. Several sample containers 58 are connected in a train-like manner. At both ends of the train a magnet 60 is arranged (only 1 magnet is shown in FIG. 3). Adjacent to the housing 71 a conveyor belt 64 which can be driven via motor driven rollers 66 is provided for. On this conveyor belt, two magnets 62 (again only one is shown) are arranged. The distance between the two magnets 62 and the distance between the magnets 60 is the same. Furthermore, the distance between the magnets 60 and their arrangement is such that the train of containers 58 is in a completely extended location, i.e. without any slack. By moving the conveyor 64 the two magnets 60 are also moved and pull the sample containers or boats 58 along with them and into the desired positions.

Reasonable variations and modifications which will become apparent to those skilled in the art can be made in this invention without departing from the spirit and scope thereof.

I claim:

1. An apparatus for measuring the amount of a fluid adsorbed by each of a plurality of samples comprising
    (a) an adsorption zone provided with means for exposing the plurality of samples to said fluid,
    (b) a desorption zone provided with means for causing the release of at least some of the adsorbed fluid from one of said sample present in said desorption zone,
    (c) a detector operatively connected to said desorption zone and capable of detecting the fluid released from said sample and generating a signal representative of the quantity of said released fluid,
    (d) transporting means built and operatively associated with said adsorption zone and said desorption zone to allow the transportation of the samples from said adsorption zone to said desorption zone,
    (e) housing means enclosing said adsorption zone and said desorption zone and separating both from uncontrolled contact with the surrounding atmosphere,
    (f) connecting means between said adsorption zone and said desorption zone enabling the transporting of said samples from said adsorption zone to said desorption zone, isolated from uncontrolled connection with the atmosphere, and providing for sufficient thermal insulation between said adsorption zone and said desorption zone.

2. An apparatus in accordance with claim 1 further comprising a drying zone within said housing means.

3. An apparatus in accordance with claim 1 wherein said housing is an elongated chamber containing in its first end section the drying zone, and in its second end section the adsorption zone and containing the desorption zone between these two zones.

4. An apparatus in accordance with claim 3 wherein a first conduit is attached to the first end of said elongated housing, a second conduit is attached to the second end of said elongated housing and wherein these conduits are in fluid communication with the interior of said housing and thus with the three zones.

5. An apparatus in accordance with claim 4 wherein said first conduit is connected to a source of carrier gas and adsorbing fluid and said second conduit is operatively connected to said detector.

6. An apparatus in accordance with claim 4 further comprising a third conduit communicating with the interior of said housing at the location of said desorption zone.

7. An apparatus in accordance with claim 6 wherein both said first and said second conduit are connected to a source of carrier gas and adsorbing fluid and wherein said third conduit is operatively connected to said detector.

8. An apparatus in accordance with claim 2 wherein said drying zone comprises first heating means and said desorption zone comprises second heating means.

9. An apparatus in accordance with claim 1 wherein said transporting means comprises:
    (a) guiding means for allowing a directed movement inside of said housing for a plurality of sample holders,
    (b) initiating means for initiating said directed movement outside of said housing.

10. An apparatus in accordance with claim 9 wherein said guiding means comprise a sliding surface allowing said sample holders to be moved in the form of a sample holder train within said housing,
   wherein at least one magnet is arranged for directed movement within said housing and
   wherein said initiating means comprises at least one further magnet arranged outside of said housing in close proximity outside of said housing in close proximity with said one magnet inside of said housing so that the movement of the outside magnet (or magnets) causes a directed movement of the inside magnet (or magnets) and the sample holders associated therewith.

11. An apparatus in accordance with claim 1 comprising controller means having at least one input and at least one output said input being operatively connected to said detector for receiving said signal and said output being operatively connected to said transporting means for controlling the movement of the samples within the housing.

12. A process for determining the quantity of a fluid adsorbed by each of a plurality of samples comprising the following steps
   (a) introducing said plurality of samples into a housing separating the entirety of the plurality of samples from uncontrolled contact with the surrounding atmosphere,
   (b) subjecting said samples at a low first temperature in the adsorbing zone of said housing with said fluid for a time sufficient to achieve adsorption of said fluid on said sample,
   (c) moving one of the samples into a desorption zone within said housing,
   (d) heating said one sample which is located in said desorption zone to a high second temperature to effect desorption of said fluid,
   (e) delivering said desorbed fluid to a detector,
   (f) generating a signal in said detector responsive to the quantity of fluid desorbed by the sample,
   (g) carrying out the adsorption, desorption and signal generating steps on all of the samples.

13. A process in accordance with claim 12 comprising
   (a) simultaneously contacting said plurality of samples at the low temperature in the adsorption zone with said fluid and
   (b) seriatim subjecting each individual sample to said high second temperature in said desorption zone.

14. A process in accordance with claim 12 wherein said samples are subject to the contact of a carrier gas and an adsorbing fluid, wherein said carrier gas is selected from the group consisting of hydrogen and helium and wherein said adsorbing fluid is selected from the group consisting of nitrogen, oxygen, argon, carbon dioxide, propane and n-butane.

15. A process in accordance with claim 12 wherein said samples are dried prior to the adsorption step within said housing in a drying zone and wherein the dried samples are then moved from the drying zone into the adsorption zone.

16. A process in accordance with claim 15 wherein said drying is effected by heating the samples.

17. A process in accordance with claim 12 wherein said signal is generated automatically and responsive to said signal said movement of said samples between the zones is automatically carried out.

* * * * *

UNITED STATES PATENT AND TRADEMARK OFFICE
CERTIFICATE OF CORRECTION

PATENT NO. : 4,335,610

DATED : June 22, 1982

INVENTOR(S) : Richard L. Scott

It is certified that error appears in the above—identified patent and that said Letters Patent is hereby corrected as shown below:

Claim 1, col. 6, line 12, "sample" should be --- samples ---.

Claim 3, col. 6, line 25, "1" should be --- 2 ---.

Claim 14, col. 8, line 18, "subject" should be --- subjected ---.

Signed and Sealed this

Twenty-fourth Day of August 1982

|SEAL|

Attest:

GERALD J. MOSSINGHOFF

Attesting Officer Commissioner of Patents and Trademarks